United States Patent [19]

Uchida et al.

[11] 4,205,554
[45] Jun. 3, 1980

[54] SUPERSONIC FAULT DETECTION APPARATUS

[75] Inventors: Kuniharu Uchida, Fujisawa; Yoshishige Sakurai, Yokohama, both of Japan

[73] Assignee: Tokyo Shibaura Denki Kabushiki Kaisha, Kanagawa, Japan

[21] Appl. No.: 899,214

[22] Filed: Apr. 24, 1978

[30] Foreign Application Priority Data

Apr. 26, 1977 [JP] Japan .................................. 52-47369

[51] Int. Cl.$^2$ ............................................ G01N 29/04
[52] U.S. Cl. ......................................... 73/626; 73/901
[58] Field of Search ................ 73/602, 618, 619, 620, 73/621, 625, 626, 633, 634, 901; 128/2 Y, 660

[56] References Cited

U.S. PATENT DOCUMENTS

| 3,817,089 | 6/1974 | Eggleton et al. | 73/625 |
| 3,857,052 | 12/1974 | Beller | 73/619 |
| 4,058,001 | 11/1977 | Waxman | 73/620 |

OTHER PUBLICATIONS

Young et al., "Digitally Controlled Ultrasonics For Testing Steel on Line", *Non-Destructive Testing*, pp. 131–135, Jun. 1976.

Moyer et al, "Expanding Capability of Laboratory Ultrasonic Testing Facility", *Materials Evaluation*, pp. 193–204, Oct. 1973.

Stiefeld; "A Strategy for the Use of Minicomputer-Based Test System as General Purpose NDE Laboratory Tool", *Materials Evaluation*, pp. 97–103, Jun. 1973.

*Primary Examiner*—Stephen A. Kreitman
*Attorney, Agent, or Firm*—Stevens, Davis, Miller & Mosher

[57] ABSTRACT

A probe unit including a plurality of ultrasonic fault detection probes is moved along an object to be examined by a probe drive unit. The fault detection signals produced by the probes are transfer switched among a plurality of channels of a channel selector and the output of the channel selector is sampled by a high speed sampling device. A computer is connected to the probe drive unit, channel selector and the sampling device to apply operating signals thereto and to receive the outputs thereof.

6 Claims, 16 Drawing Figures

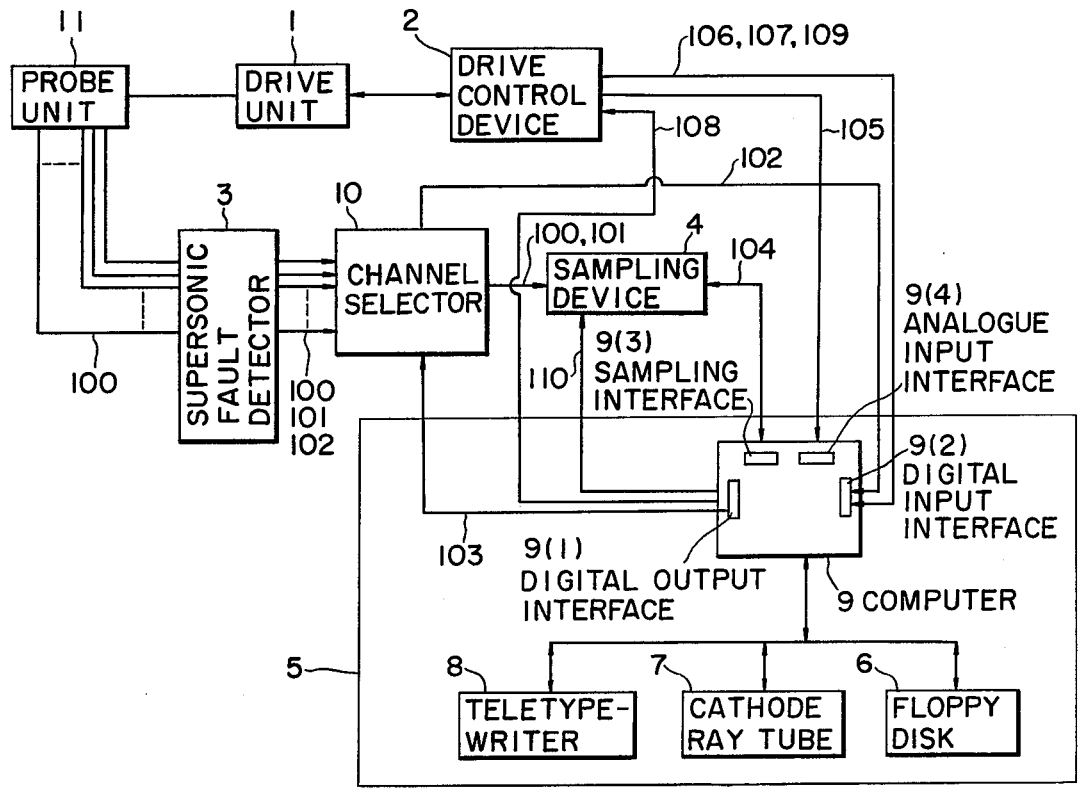
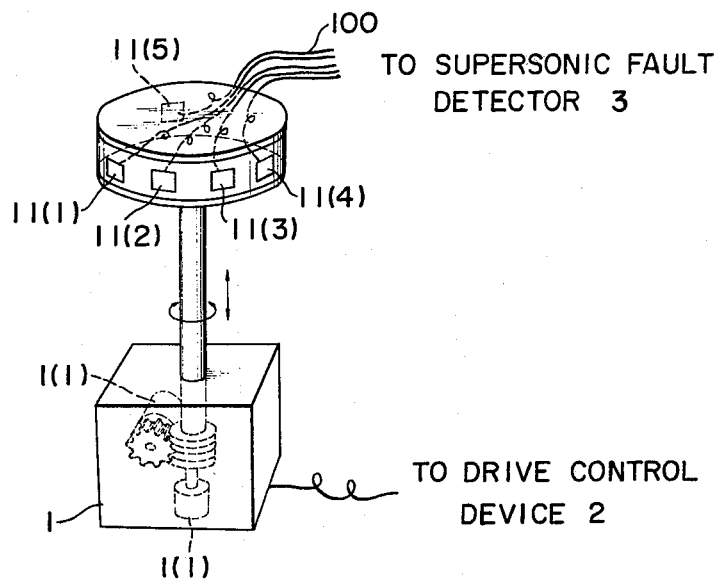

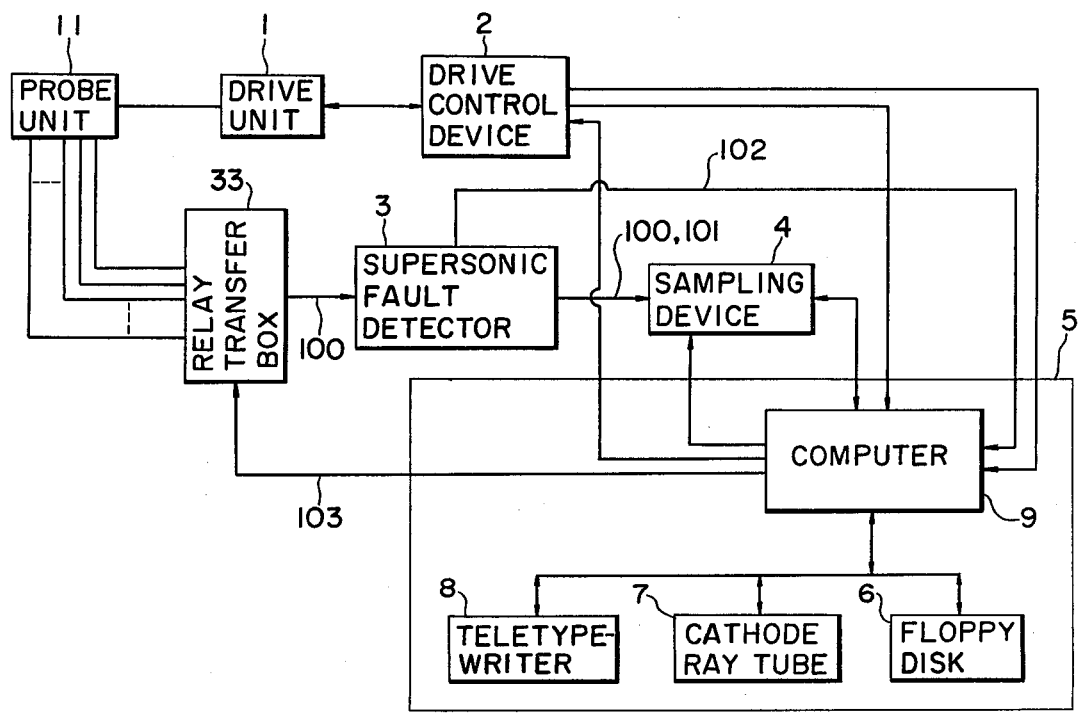
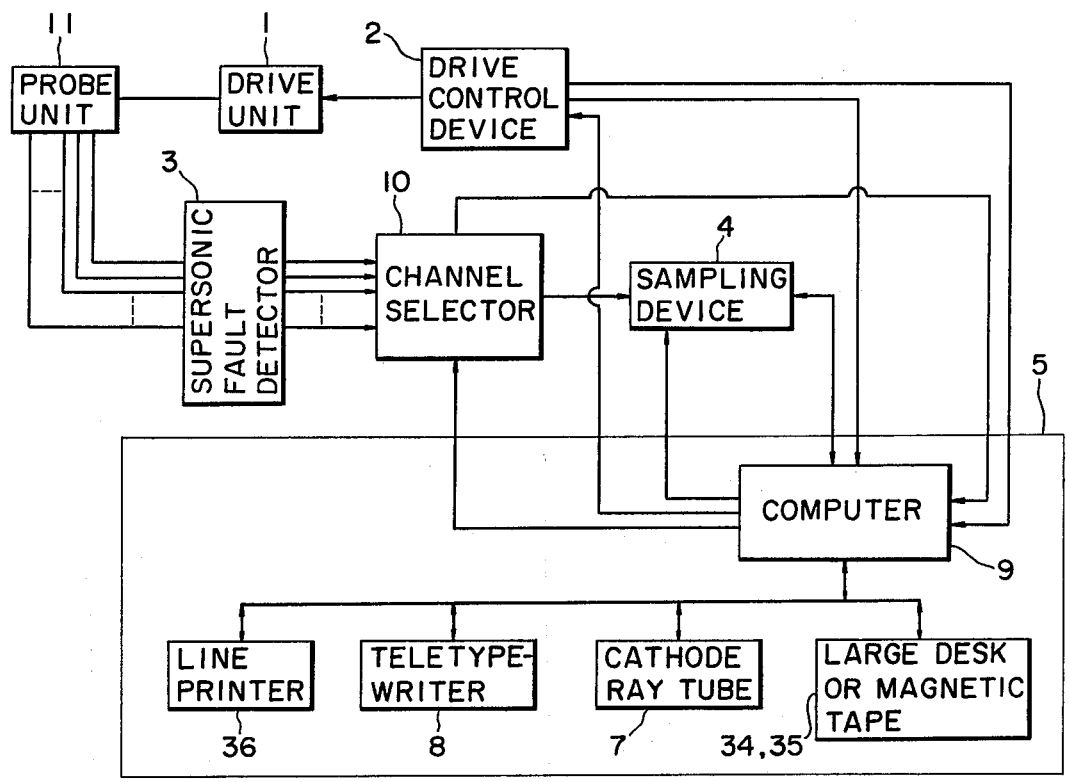

SUPERSONIC FAULT DETECTION APPARATUS

BACKGROUND OF THE INVENTION

This invention relates to supersonic fault detection apparatus capable of simultaneously detecting faults or defects by means of a plurality of supersonic probes and comparing and evaluating the results of the detection by an electronic computer.

Supersonic fault detection test is generally carried out with a single probe, but with such device it is impossible to accurately detect the position and orientation of the fault in an object to be tested. For this reason, in order to precisely determine the distribution of the faults it is necessary to use a number of probes so as to compare and analyze the test results. Furthermore, as the path and attenuation of the supersonic beam differ depending upon the shape and material of the object it is necessary to evaluate the position and size of the fault by taking into consideration the effects of these factors.

However, as the data regarding the result of supersonic fault detection are abundant it is difficult to compare and investigate the data obtained by using a plurality of probes by taking into consideration the material of the object and the characteristic of the probe. According to one example of the method of simultaneously detecting faults by using a plurality of probes, two probes are moved simultaneously along both sides of a portion of the object which is expected to contain faults, for example, a weld seam of a pipe. With this method, however, it is not only impossible to compare the test data of three or more probes but also impossible to separately evaluate defects which extend along the paths of more than two supersonic beams. In such a case, only the largest fault is detected. Where the supersonic beam paths of two probes are different, that is, where the probes have different characteristics and where it is necessary to consider the attenuation of the supersonic wave, it is impossible to correctly evaluate the distribution of the faults.

SUMMARY OF THE INVENTION

It is an object of this invention to provide an improved supersonic fault detection apparatus capable of decreasing the examination time of the faults by using a number of supersonic probes which are moved simultaneously.

Another object of this invention is to provide a novel supersonic fault detection apparatus capable of accurately judging and evaluating the shape and size of the faults by a computer.

According to this invention, there is provided supersonic fault detection apparatus comprising a plurality of probes for transmitting and receiving a supersonic wave, probe drive means for simultaneously moving the plurality of probes over the same distance, a supersonic fault detector which transmits and receives at a predetermined interval fault detection signals produced by the probes, a channel selector for transfer switching output signals of the supersonic fault detector with a digital signal, and sampling means for sampling and storing the output signal of the channel selector.

BRIEF DESCRIPTION OF THE DRAWINGS

This invention can be more fully understood from the following detailed description taken in conjunction with the accompanying drawings in which:

FIG. 1 is a block diagram showing one example of the supersonic fault detection apparatus embodying the invention;

FIG. 2 is a perspective view showing the probes and the probe drive unit shown in FIG. 1;

FIGS. 6a, 7 through 10 are block diagrams showing another embodiments of this invention; and FIG. 6b is a graph useful to explain the operation of the modification shown in FIG. 6a.

DESCRIPTION OF THE PREFERRED EMBODIMENTS

Figure 3A:
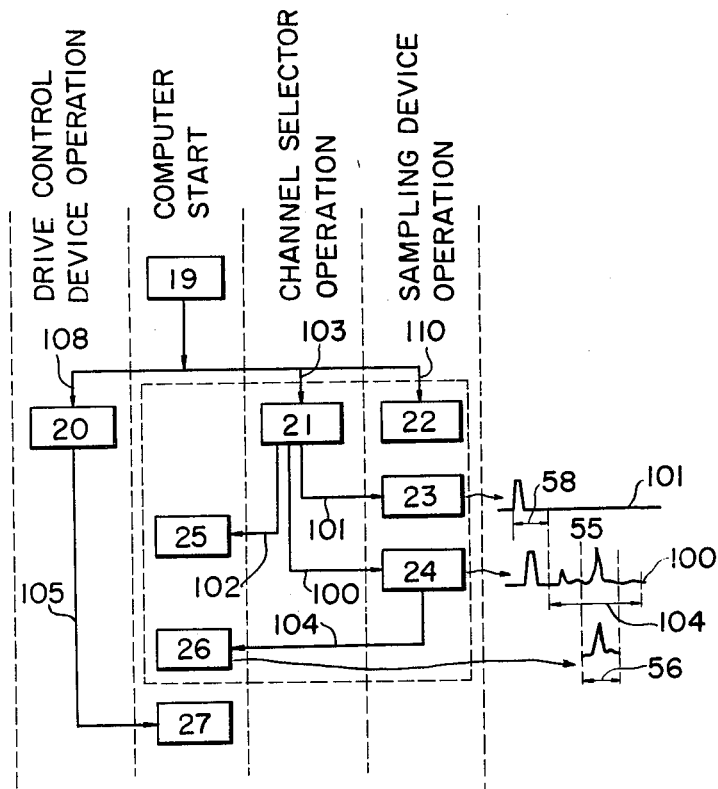
FIG. 3a is a block diagram and FIG. 3b are graphs which are useful to explain the operation of the supersonic fault detection device of this invention.

As shown in FIG. 2, the supersonic fault detection apparatus of this invention comprises a probe unit 11 containing a plurality of supersonic probes 11(1) through 11(5), a probe drive unit 1 driven by a pulse motor 1(1) and connected to the probe unit 11 through a shaft for simultaneously moving the probes, and a drive control device 2 electrically connected to the drive unit 1 for moving the probe unit 11 according to a predetermined pattern set by a digital switch not shown.

As shown in FIG. 1 the fault detection signals produced by probes 11(1) through 11(5) are applied to a multichannel supersonic detector 3 which is constructed to send a supersonic pulse to each probe and to receive a pulse reflected by a fault in the object to be examined at an interval of about 200 Hz. With the detector 3 constructed in this manner, it is possible to prevent interference between ultrasonic signals.

The output signal of the supersonic fault detector 3 is applied to an 8 channel selector 10 which is transfer switched by a digital signal 103 supplied from a computer 9. In addition to amplified detection signals 100, a synchronizing signal 101 utilized to provide a beam path reference time and a coupling check signal 102 utilized to judge that whether the probes of the probe unit 11 are intimately in contact with the object or not are also supplied to the channel selector 10. Accordingly, the fault detector 3 is coupled with the channel selector 10 through 15 signal lines where 5 probes are used.

In response to a 3 bit binary signal 103 provided by the computer through its digital output interface 9(1) the channel selector 10 operates to switch the detection signals 100 produced by respective probes, the synchronizing signal 101 and the coupling check signal 102 so as to apply the detection signal 100, and the signal 101 of a specific probe to a high speed sampling device 4 and to apply signal 101 to a digital input interface 9(2) of the computer.

The high speed sampling device 4 is constituted by a wave memory device or a transient recorder and functions to convert the analogue detection signal into a storable digital quantity of 7 or 8 bits at about 1024 to 4096 points at a predetermined interval of from about 0.01 μsec. to 1 ms with a preset time delay of 0~±2 ms with reference to an instant at which the synchronizing signal is applied. The output of the high speed sampling device 4 is applied to a sampling interface 9(3) and the digital output interface 9(1) of the computer. The sampling interface 9(3) enables to store in a memory device thereof any number of continuous points of about 1000 points of the detection signal converted into the digital quantity in accordance with an instruction of the computer.

The two dimensional movement of the probe unit 11 is converted into an analogue voltage 105 by a potentiometer (not shown) contained in the drive unit 1, and the analogue voltage is supplied to an analogue input interface 9(4) of the computer through the drive control device. When the probe unit is moved a pulse signal 106 representing a definite amount of movement in each direction of movement and pulse signal 107 which is generated when the direction of movement of the probe unit is changed are applied to the digital input interface 9(2) of the computer 9. Furthermore, a line carrying a digital signal 108 for instructing start and stop of the probe unit and a line carrying a digital signal 109 representing the running or stop state of the probe unit are coupled to the digital output interface 9(1) and the digital input interface 9(2) respectively.

In addition to various interfaces 9(1)–9(4) described above, the computer system 5 further comprises a floppy disk 6 to store data judged to be effective by a computer program among the detected data, a cathode ray tube 7 which displays the defects which are determined by processing the effective data by the computer and a teletypwriter 8 for printing out the data inputs and the effective data into and out of the computer program. The floppy disk, the cathode ray tube and the teletypewriter are connected to the computer 9 through signal lines so that these peripheral devices are controlled in accordance with a predetermined program of the process control unit of the computer 9.

As shown in FIG. 3a when the computer program is started at step 19 a start signal 108 is applied to the drive control device at step 20, a digital signal is applied to channel selector 10 at step 21 so to effect switching of the supersonic fault detection signal to the probe, the synchronizing signal and the coupling check signal according to a prescribed program. Furthermore, a digital signal 110 for preparing sampling is applied to the high speed sampling device from the computer at step 19.

Figure 3B:
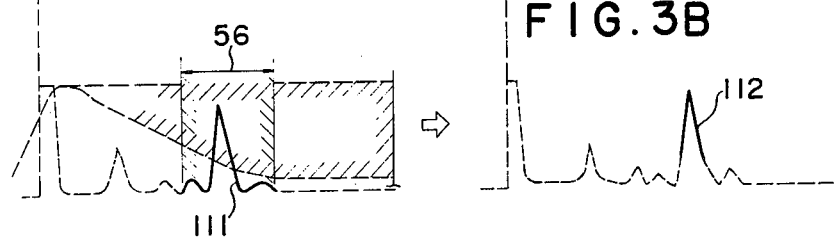

Upon completion of these procedures, and when the synchronizing signal 101 is applied to the high speed sampling device 4 from the channel selector 10, detection signal is sampled a definite time after (shown by 58 in FIG. 3a and set by the high speed sampling device) and then the sampled signal is converted into a digital detection signal 104 which is stored in the sampling device 4 at step 24. During this time the computer receives the coupling check signal at step 25, and at the same time when the detection signal of a given probe has sampled, the interface for the high speed sampling device reads out the data 104 which has been stored in the sampling device to store (at step 26) the data during an interval 56 preset by the program, that is, the fault depth (the length of the beam path) in a memory device of the interface for the high speed sampling device. The range of the stored data is set in a range necessary to detect faults by the probes determined by an input from the teletypewriter. Upon completion of these steps, the computer again supplies the digital signal and the sampling preparation signal to the high speed sampling device at steps 21 and 22 and the connection is switched to another probe according to the program. Then, by similar operations data are stored at step 25 in the memory device of the interface for high speed sampling. By repeating these operations for all probes according to the program, the data regarding the movement or new position of the probe unit is applied (at step 27) to the computer through the analogue input interface from the control device 2. The time required for these operations is about 0.1 sec. Immediately thereafter the data in the memory device of the interface for the sampling device is compared with an attenuation characteristic curve of the supersonic wave previously supplied by the teletypewriter. FIG. 3b shows one example of comparing a portion of the data 111 stored in the memory device of the interface with the attenuation characteristic curve (shown by dotted lines) and data 112 larger than the attenuation characteristic curve is stored in the memory device of the computer as an effective data.

When a series of data of one cycle is stored and when the probe unit 11 moves a distance prescribed by the program, new fault detection data are sequentially stored in the computer.

The effective data stored in the memory device of the computer are transferred to the floppy disk 6 before the memory device saturates or the direction of movement of the probe unit changes. Then the computer sends a digital signal to the drive control device to stop the probe unit 11. When the transfer of the data to the floppy disk 6 is completed the computer transmits again the digital signal to resume the drive.

Figure 4A:
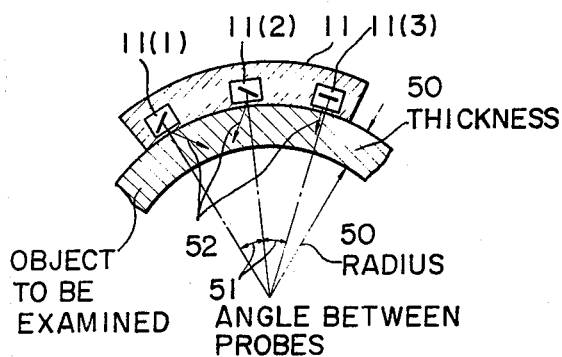
FIGS. 4a and 4b are diagrammatic representation and curves showing the data to be stored in a computer.
Figure 4B:
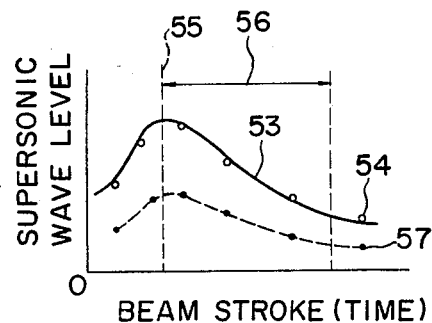

When the probe unit 11 reaches a fault detection end point set by the digital switch of the drive control device 2 a digital signal 109 representing the termination is supplied from the control device to the computer thus terminating the fault detection test. Before starting the test, items to be recorded with reference to the test and the object to be tested are sent to the memory device of the computer and the floppy disk 6 from the teletypewriter. As shown in FIGS. 4a and 4b the test data involves the shape 50 of the object to be tested, the relative position or angular relationship 51 of the probes, the identification numbers of respective probes, the order of storing the detection data, the travelling speed of the supersonic wave, the direction of movement of the probe unit, angle 52 of the supersonic wave, the length of the path of the supersonic wave and an attenuated level points 54 necessary to approximate attenuation characteristic curve 53 of the supersonic wave of each probe, a test start point 55 of a range to be tested, the travel 56 of the supersonic wave beam, and the limits (%) of the attenuation characteristic level which are necessary to isolate the effective data from unnecessary data. These data are applied to the computer to approximate a limit attenuation characteristic curve 57 as shown by dotted lines in FIG. 4b by multiplying curve 53 by above mentioned limits (%). Further, to set the timing of detecting the fault detection signal, the data regarding the pitch of the movement of the probe unit are also applied to the computer so as to apply the fault detection signal to the computer each time the probe moves over a preset pitch.

The fault detection data recorded in the floppy disk are typed out by the teletypewriter or displayed by the cathode ray tube according to the program during the test of after the test.

Figure 5A:
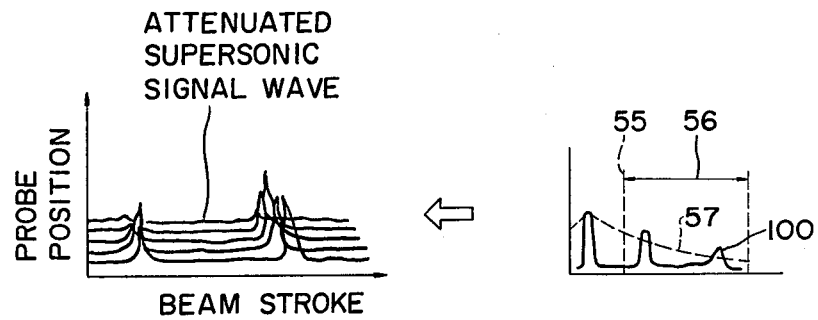
FIGS. 5a through 5d are graphs showing a method of displaying the detected faults.

FIG. 5a shows a record of a three dimensional A scope display in which the relationship between the variation in the A scope display (the detection signal level and the beam stroke) and the position of the probe is displayed, as one example of displaying the defects.

Figure 5B:
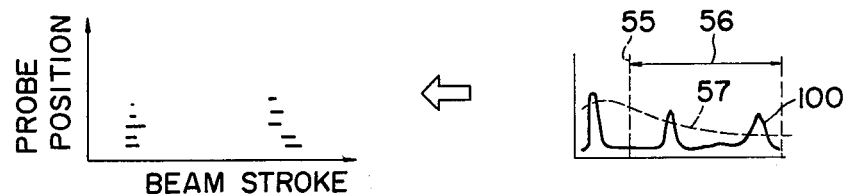
Figure 5C:
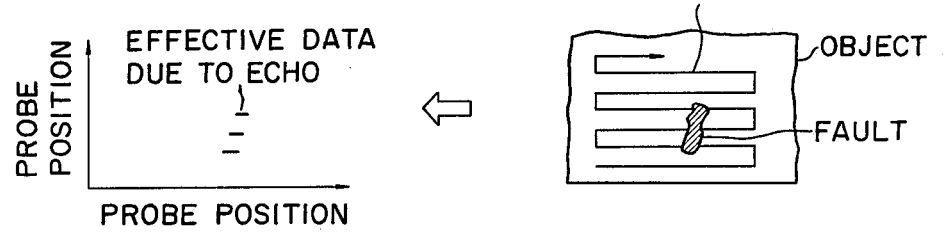

FIG. 5b shows a B scope display showing the relationship between the beam stroke and the position of the probe unit which represents signals exceeding the limit level and FIG. 5c shows a C scope display showing the relationship between the two dimensional position of the probes in the probe unit and the effective signal above the limit level 57.

Figure 5D:
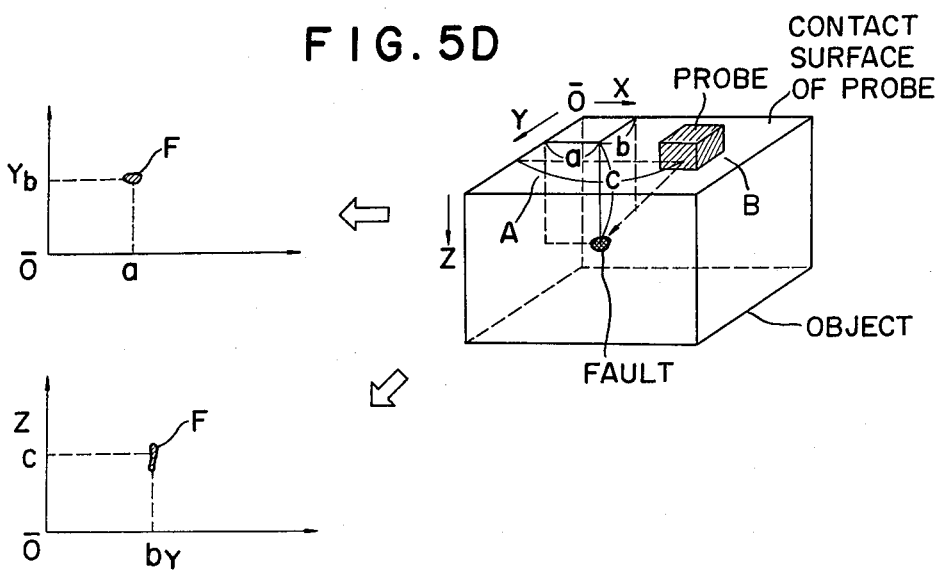

As shown in FIG. 5d, when a defect F is detected by transmitting a supersonic wave from a probe at a predetermined velocity and predetermined angles with respect to X, Y and Z axes of the object, the position (a,b,c) of the defect is calculated from the positions A and B of the probe and the travelling speed and angle of the supersonic wave, and the position of the defect in the X-Y, or Y-Z or X-Z plane is displayed by the cathode ray tube. The method of display described above makes it to display any position of the probe, any beam path and any area of the object.

Figure 6A:
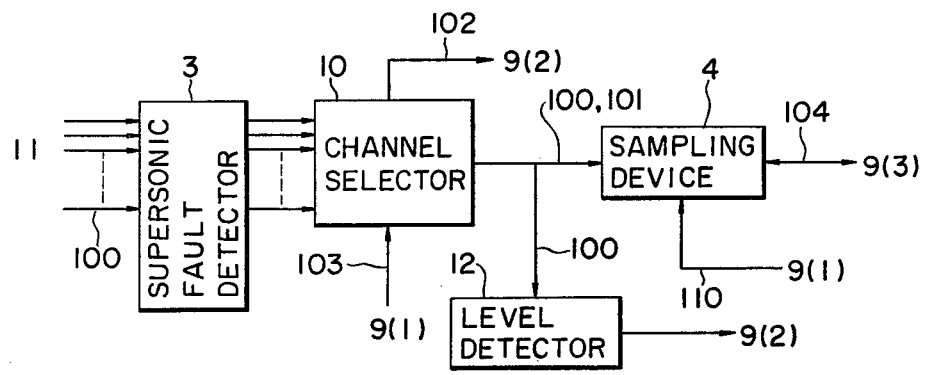
Figure 6B:
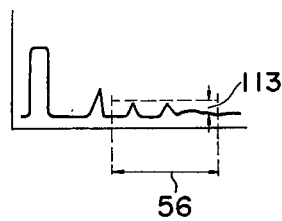

In a modified embodiment shown in FIG. 6, a level detector 12 controlled by the computer is provided. When the maximum echo level in a predetermined range 56 of the detection signal exceeds a preset level 113, this detector 12 permits the high speed sampling device to detect the fault detection signals whereas when the maximum echo level is lower than the preset level the detector 12 prevents the high speed sampling but the operation is advanced to the next step. With this modification, it is possible to reduce the processing time of the computer. When the attenuation characteristic curve of the supersonic wave is set by hardwares so as to judge the effective data before high speed sampling it is also possible to decrease the processing time of the computer.

Figure 7:
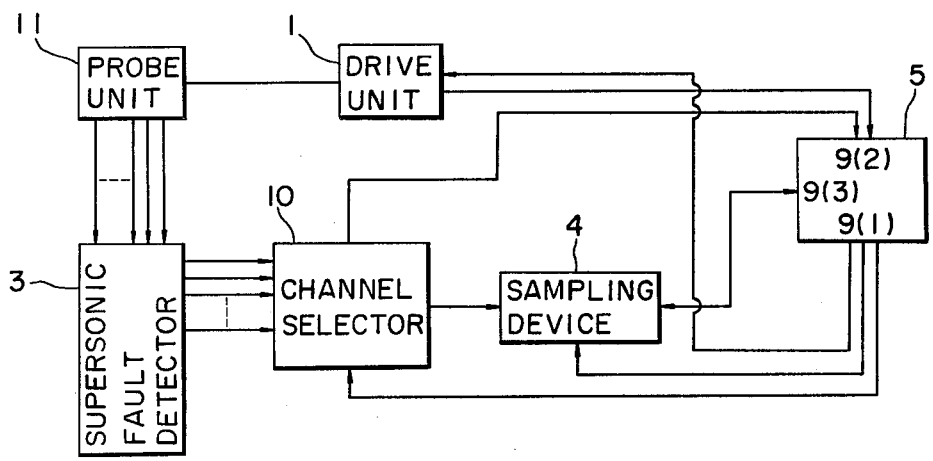

In another embodiment shown in FIG. 7, the probe drive unit 1 is directly controlled by the computer. In this modification, it becomes possible to substitute a display device of the probe for the drive control device. Furthermore, it becomes possible to apply the data representing the position of the probe unit to the computer in the form of a binary coded decimal signal or a binary digital signal and to compute the position of the probe unit by the computer program.

In a modification shown in FIG. 8, instead of using the channel selector 10 for sampling the detection signal at a high speed a relay transfer box 33 is connected between a probe and a supersonic fault detector 3. With this construction, a conventional one channel supersonic fault detector can be used.

In the modification shown in FIG. 9, instead of the floppy disk, a large disk 34 or a magnetic tape 35 is used for storing the data in the computer, and a line printer 36 is added to print the data.

Figure 10:
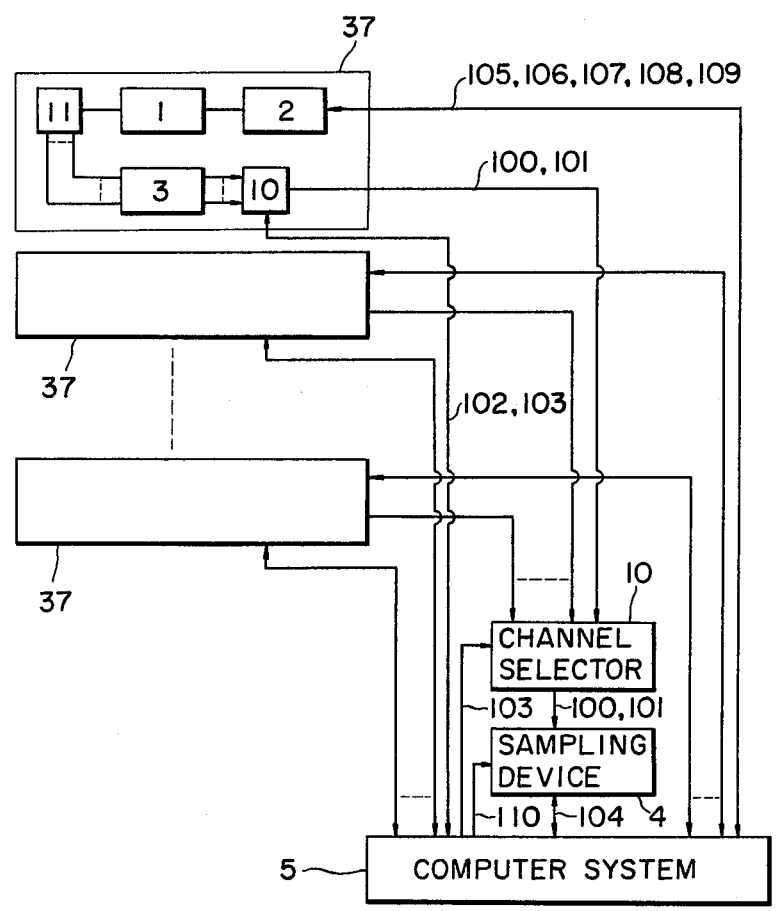

In the embodiment shown in FIG. 1 where the high speed sampling device has a large memory capacity it is possible to directly judge by the computer that whether the data of respective probes are effective or not without storing the data in a buffer memory device. By increasing the calculating speed and the capacity of the computer it is possible to increase the number of the probes from 5 to about 50 and to simultaneously examine a number of objects. In this case, it is necessary to use a plurality of combinations 37 each including a probe drive unit, a supersonic fault detector, etc. and to store a fault test data as shown in FIG. 10.

As has been described above, according to this invention, since the fault detection is made by a plurality of probes which operate simultaneously it is not only possible to decrease the detection time but also to readily and accurately compare the detection data produced by respective probes thereby decreasing erroneous judgement and evaluation. Moreover, as the judgement and evaluation of the faults are made by taking into consideration the attenuation of the supersonic wave during travelling it is possible to increase the accuracy of evaluation for the shape and size of the fault.

What is claimed is:

1. Supersonic fault detection apparatus comprising a plurality of probes for simultaneously transmitting and receiving a supersonic wave in different directions, probe drive means for simultaneously moving said plurality of probes over the same distance, a supersonic fault detector which transmits and receives at a predetermined interval fault detection signals produced by said plurality of probes, a channel selector for transfer switching output signals of said supersonic fault detector with a digital signal, sampling means for sampling and storing the output signal of said channel selector, and an electronic computing means adapted to compare data stored in said sampling means with a predetermined attenuation curve.

2. The supersonic fault detection apparatus according to claim 1 wherein said electronic computer is connected to supply said digital signal to said channel selector, to receive a signal from said channel selector indicating that whether said probes are maintained in intimate contact with an object to be examined or not, to receive a signal from said probe drive means representing movement and operation conditions thereof, to transmit a signal to said probe drive means for operating the same and to receive the output signal of said sampling means.

3. Supersonic fault detection apparatus comprising a probe unit including a plurality of probes for simultaneously transmitting and receiving a supersonic wave in different directions, a probe drive unit mechanically coupled to said probe unit for moving and rotating the same along an object to be examined, a drive control device for electrically controlling said probe drive unit and generating a signal representing movement and operating conditions thereof, a supersonic fault detector which receives from said plurality of probes fault detection signals at a predetermined interval, a channel selector connected to receive the output of said supersonic fault detector for transfer switching the output signals of said supersonic fault detector among a plurality of channels, sampling means for sampling and storing the output signal of said channel selector and computer connected to supply operating signals to said drive means, and to receive the outputs of said drive control device and said sampling means, said electronic computer being adapted to compare data stored in said sampling means with a predetermined attenuation curve.

4. The supersonic fault detection apparatus according to claim 3 which further comprises means responsive to the output of said channel selector for controlling the operation of said sampling means depending upon the level of said fault detection signals.

5. Supersonic fault detection apparatus comprising a probe unit including a plurality of probes for simultaneously transmitting and receiving a supersonic wave in different directions, a probe drive unit mechanically coupled to said probe unit for rotating and moving the same along an object to be examined and including means for generating a signal representing movement and operating conditions of said probe drive unit, a supersonic fault detector which receives from said plurality of probes fault detection signals at a predetermined interval, a channel selector connected to receive the output of said supersonic fault detector for transfer switching the output signals of said supersonic fault detector among a plurality of channels, sampling means for sampling and storing the output signal of said channel selector, and a computer connected to supply operating signals to said probe drive unit, said channel selector and said sampling means, and to receive the outputs of said probe drive unit and sampling means, said electronic computer being adapted to compare data stored in said sampling means with a predetermined attenuation curve.

6. Supersonic fault detection apparatus comprising a probe unit including a plurality of probes for simultaneously transmitting and receiving a supersonic wave in different directions, a probe drive unit mechanically coupled to said probe unit for moving and rotating the same along an object to be examined, a drive control device for electrically controlling said probe drive unit and generating a signal representing movement and operating conditions thereof, a supersonic fault detector which receives from said plurality of probes fault detection signals at a predetermined interval, transfer relay means connected between said probe unit and said supersonic fault detector for switching the connection of said plurality of probes, sampling means for sampling the output signal of said supersonic fault detector, and a computer connected to supply operating signals to said drive control device, said transfer relay means and said sampling device and to receive the outputs of said drive control device and said sampling device, said electronic computer being adapted to compare data stored in said sampling device with a predetermined attenuation curve.

* * * * *